US007265100B2

(12) United States Patent
Roncucci et al.

(10) Patent No.: US 7,265,100 B2
(45) Date of Patent: Sep. 4, 2007

(54) SEPARATION OF REGIOISOMERS OF METAL PHTHALOCYANINES

(75) Inventors: Gabrio Roncucci, Colle Val d'Elsa (IT); Francesca Giuntini, Mercatale Val di Pesa (IT); Donata Dei, San Gimignano (IT); Maria Paola De Filippis, Firenze (IT); Paolo Sarri, Firenze (IT); Marco Possenti, Firenxa (IT); Valentina Paschetta, Ferrone (IT); Giacomo Chiti, Montemurlo (IT)

(73) Assignee: L. Molteni & C. Dei Fratelli Alitti Societa' di Esercizio S.p.A., Scandicci (IT)

(*) Notice: Subject to any disclaimer, the term of this patent is extended or adjusted under 35 U.S.C. 154(b) by 0 days.

(21) Appl. No.: 10/493,971

(22) PCT Filed: Oct. 28, 2002

(86) PCT No.: PCT/EP02/12021

§ 371 (c)(1),
(2), (4) Date: Apr. 28, 2004

(87) PCT Pub. No.: WO03/037902

PCT Pub. Date: May 8, 2003

(65) Prior Publication Data

US 2005/0009802 A1    Jan. 13, 2005

(30) Foreign Application Priority Data

Oct. 29, 2001    (EP)    .................................. 01125770

(51) Int. Cl.
| | |
|---|---|
| *A61K 31/695* | (2006.01) |
| *A61K 31/555* | (2006.01) |
| *A61K 49/10* | (2006.01) |
| *C09B 47/04* | (2006.01) |

(52) U.S. Cl. ..................... 514/63; 514/185; 514/410; 540/123; 540/131; 540/135; 540/145; 424/9.61; 424/9.362; 106/410; 502/163

(58) Field of Classification Search ................ 540/123, 540/131, 135, 145, 124, 125; 502/163; 508/296; 106/410; 430/59.4; 424/9.362, 9.61; 534/15; 514/185, 410, 63

See application file for complete search history.

(56) References Cited

U.S. PATENT DOCUMENTS

5,965,598 A * 10/1999 Roncucci et al. ........... 514/410

FOREIGN PATENT DOCUMENTS

| EP | 0 906 758 A1 | 4/1999 |
| EP | 1 164 135 A1 | 12/2001 |
| JP | 04 023868 A | 1/1992 |

OTHER PUBLICATIONS

Sommerauer et al., Separation of 2(3), ((10), 16(17), 23(24)-Tetrasubstituted Phthalocyanines with Newly Developed HPLC Phases. J.Am. Chem. Soc. 1996, 118, pp. 10085-10093.*
Uvarova et al. Porphjyrins and Phthalocyanines in High Performance Liquid Chromatography. J. Anal. Chem. 2000, 55(10) pp. 910-925.*
Hanack et al. Separation of Structural Isomers of Tetra-tert-butylphthalocyaninatonickel. Angew. Chem. Int. Ed. 1993, 32(10) pp. 1422-1424.*
Roncucci et al. U.S. Appl. No. 10/311,663, filed Dec. 16, 2002.*
Roncucci et al. U.S. Appl. No. 10/472,882, filed Apr. 1, 2004.*
Roncucci et al. U.S. Appl. No. 10/548,793, filed Sep. 12, 2005.*
Roncucci et al. U.S. Appl. No. 10/512,287, filed Oct. 25, 2004.*
Uvarova et al. "Porphyrins and phthalocyanines in high-performance liquid chromatography." J. Anal. Chem. 2000, 55(10), 910-925.*
Brasseur, N. et al., "Synthesis and Photodynamic Activities of Silicon 2,3-Naphthalocyanine Derivatives," J. Med. Chem. 37:415 (1994).
Gorlach, B. et al., "Separation of 2(3), 9(10), 16(17), 23(24)-Tetraalkoxy-Substituted Phthalocyanines With a C30 HPLC Phase," First Int'l. Conf. on Porphyrins and Phthalocyanines, Dijon France (Jun. 25-30, 2000).
Hanack, M. et al., "Chromatographic Separation of the Four Possible Structural Isomers of a Tetrasubstituted Phthalocyanine:

Tetrakis(2-Ethylhexyloxy)-Phthalocyaninatonickel(II)," Angew. Chem. Int. Ed. Engl. 32(10):1422 (1993).

Hanack, M. et al., "Separation of Structural Isomers of Tetra-*tert*-Butylphthalocyaninatonickel(II)," J. Chem. Soc. Chem. Comm. p. 58 (1993).

International Search Report, from PCT/EP02/12021, mailed Mar. 25, 2003.

Leznoff, C. et al., "The Synthesis of Phthalocyanines at Room Temperature," Chem. Comm. p. 1245 (1996).

Leznoff, C. et al., "The Syntheses of 2,9,16,23- and 1,8,15,22-Tetrahydroxyphthalocyanines," Can. J. Chem. 72:1990 (1994).

Sommerauer, M. et al., "Separation of 2(3), 9(10), 16(17), 23(24)-Tetrasubstituted Phthalocyanines With Newly Developed HPLC Phases," J. Am. Chem. Soc. 118:10085 (1996).

Uvarova, M.I. et al., "Porphyrins and Phthalocyanines in High-Performance Liquid Chromatography," J. Analytical Chem. 55(10):910 (2000).

* cited by examiner

*Primary Examiner*—Devesh Khare
(74) *Attorney, Agent, or Firm*—Wolf, Greenfield & Sacks, P.C.

(57) ABSTRACT

The present invention refers to a process for the separation of regioisomeric mixtures of metal phthalocyanines of formula (I), to the regioisomers obtained by this process, and their use as phototherapeutic and photodiagnostic agents

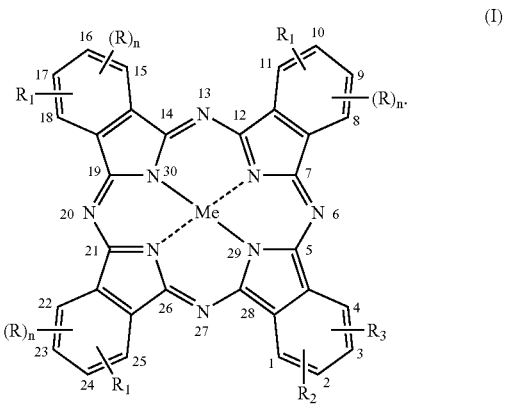

16 Claims, 10 Drawing Sheets

SEPARATION OF REGIOISOMERS OF METAL PHTHALOCYANINES

RELATED APPLICATIONS

This application claims priority to PCT Application No. PCT/EP02/12021, filed Oct. 28, 2002, which claims priority to European Patent Application No. 01125770.6, filed Oct. 29, 2001.

FIELD OF THE INVENTION

The present invention refers to a separation process of regioisomers of metal phthalocyanines of formula (I) hereinafter reported, which are photosensitizers characterized by absorption and fluorescence in the red region of the visible spectrum.

STATE OF THE ART

The phthalocyanine chromofluorophore macrocycles are known to produce reactive species of oxygen, in particular singlet oxygen or radicals, by interacting with visible light. Compounds having a basic phthalocyanine structure are under development for a perspective use in photodynamic therapy (PDT) and/or for diagnostic purposes as well as for many other interesting applications which span over a wide range of technological fields. In particular Zn(II)-phthalocyanines and their conjugates have been recently described in the U.S. Pat. No. 5,965,598, in the European Patent Application No. 00112654.9, and in the European Patent Application No. 01106411.0, all in the name of the Applicant.

Even limiting the discussion to the field of PDT, phthalocyanines represent one of the most interesting type of photosensitizers, suitable for a variety of applications, and also suitable for the preparation of "second generation photosensitizers" for the therapeutic application against tumor and iperproliferative diseases as well as for antimicrobial and biocidal purposes.

In the scientific literature it has been recently reported that not only the number and charge of substituents present on the photosensitizers moieties affect the in vitro and in vivo phototoxicity of the compounds (N. Brasseur et al. *J. Med. Chem.* 1994, 37, 415-420), but also that the non-optimal distribution and the poor selectivity of first generation photosensitizers is related to physical-chemical features of photosensitizers, thus being related to their chemical structures too.

Phthalocyanines photosensitizers can be prepared according to procedures known in the art, such as those described in C. C. Leznoff in Phthalocyanines. Properties and Applications, Vols. I-III (Ed: A. B. P. Lever), VCH Publishers, New York, 1989.

For either some non centrosimmetrical phthalocyanines or for tetra substituted phthalocyanine the conventional statistical organic synthesis lead to the preparation of a mixture of regioisomers, the composition of which has been reported to be dependent from either substituents and coordinating metal.

The statistic condensation in the tetrasubstituted phthalocyanines synthesis, favors, in absence of other driving factors, the formation of the less symmetric isomers and a mixture composed by 12.5% of $D_{2h}$, 25% of $C_{2v}$, 50% of $C_s$ and 12.5% of $C_{4h}$ is expected.

For the purpose of producing reactive oxygen species there is no problem in having an isomeric mixture, but in many other cases where either a site or a ligand recognition, molecular hydrophylic/hydrophobic characteristics related to efficacy apply, or finally in the case of therapeutic development, it is fundamental to have single characterized isomers.

For the previously reported examples, a selective purification is always necessary in order to obtain the single regioisomers. Several research groups have attempted at obtaining pure isomers directly by regioselective synthesis, but in this way only the $C_{4h}$ isomer of 1(4),8(11),15(18),22(25) tetrasubstituted phthalocyanines with hindering groups has been obtained (C. C. Leznoff et al. *Can. J. Chem.* 1994, 72,1990-1998; Ibid. *Chem. Commun.* 1996,1245).

An attempt at purifying metal phthalocyanine derivatives have also been recently undertaken, however very few papers concerning this matter have been published. $C_{2v}$ and $C_s$ isomers of 2(3),9(10),16(17),23(24) tetra-tert-butylphthalocyaninato Ni(II) have been enriched with silica HPLC and MPLC (M. Hanack et al *J. Chem. Soc., Chem. Commun.* 1993, 58-60).

A complete separation was achieved for a 1(4),8(11),15(18),22(25) alkyloxy-substituted Ni(II) phthalocyanine by HPLC and MPLC using, respectively, a nitrophenyl and a silica stationary phase (M. Hanack et al. *Angew. Chem.* 1993, 32,1422-1424).

Furthermore, the separation of 2(3),9(10),16(17),23(24) alkyloxy-substituted (Ni(II), Cu(II) or Zn(II)) phthalocyanines requires a purposely developed HPLC phase, that cannot be scaled, according to M. Sommerauer et al. *J. Am. Chem. Soc.* 1996, 118,10085-1Q093. B. Gorlach et al. ICPP-1 2000, Post 413; this stationary phase is in fact prepared starting from commercially available silica gel, which is then subjected to at least two reactions, with 4-aminobutyl-dimethylmethossisilane then with 2-phenylquinoline-4-carboxylic acid, in order to introduce particular spacer chains into silica. Such a procedure, besides being expensive, does invalidate the reproducibility of this stationary phase.

The isomers of the Cu(II) complex of a nitrophenoxy tetrasubstituted phthalocyanine have been also separated by HPLC with the use of a RP-$C_{18}$ column (M. I. Uvarova et al. *J. Anal. Chem.* 2000, 55,910-925).

In conclusion, up to now suitably devised chromatographic phases were needed in order to separate regioisomers of metal phtalocyanines, and conditions suitable for separation either on a small or large scale have not yet been found, in particular for Zn phtalocyanines bearing amino groups.

It is therefore felt the need of developing processes of separation of regioisomers, suitable for both laboratory and large scale preparation.

SUMMARY OF THE INVENTION

In spite of what reported in the above cited literature about the previous studies on the phthalocyanine regioisomers seperation, the Application has surprisingly found that by means of a chromatographic column separation method on standard stationary phases, such as commercially available silica and aluminium oxide, and with appropriate elution phases, an optimal resolution of regioisomeric mixtures deriving from substitution in specific positions of the phthalocyanine macrocycle, can be carried out with a variety of amino substituted phthalocyanines, in particular of Zn(II) amino substituted phthalocyanines.

Despite the presence of zinc and of the amino groups on the peripheral positions of the phthalocyanine framework, that usually cause severe tailing effects in the chromatographic behaviour, the present process proved to be efficient in the separation of phtalocyanines of formula (I), even on standard stationary phases. The Applicant has moreover found that it is possible to determine the elution order, and consequently to obtain also regioisomeric mixtures enriched in the less symmetric isomers ($C_{2v}$ and $C_s$).

Object of the present invention is therefore the process for the separation of regioisomeric mixtures of metal-phthalocyanines of general formula (I)

(I)

wherein
Me is selected from the group consisting of Zn, Si(OR$_4$)$_2$, Ge(OR$_4$)$_2$ and AlOR$_4$, wherein R$_4$ is chosen from the group consisting of H and C$_1$-C$_{15}$ alkyl;
n=0, 1;
R and R$_1$ are selected from substituents of general formula (II)

(II)

wherein
X is selected from the group consisting of O, S, NHCO, —CH$_2$—, C=C and C≡C;
Z is selected from phenyl, aryl, arylalkyl and cycloaliphatic groups; and
Y and Y', equal or different from each other, are selected from C$_1$-C$_{15}$ alkyl groups;
q=0, 1;
R$_2$ and R$_3$ are selected from H and substituents of general formula (II) as defined above, with the proviso that:
at least one of R$_2$ and R$_3$ is always other than H; and
when n=0:
a) R$_2$ and R$_3$, same or different from each other, are both different from H, or
b) R$_2$=H and R$_3$ is same or different from R$_1$;
and of pharmaceutically acceptable salts thereof;
said process consisting in a chromatographic separation comprising the following steps:
i) applying the mixture to a separation column containing the stationary phase comprising a solid support;
ii) separating said mixture by eluting the said column with the mobile phase comprising an organic solvent.

Further subject of the present invention are the separated regioisomers C4h, D2h, C2v and Cs of the metal phtalocyanines of formula (I) in substantially pure form, as well as the mixture of regioisomers C2v and Cs of the metal phtalocyanines of formula (I) in substantially pure form.

Further subject of the invention are the novel metal phtalocyanines of formula (I) wherein n=0 and R$_2$ and R$_3$ are both different from H.

Features and advantages of the present process for the separation of the regioisomeric mixtures of phtalocyanines of formula (I) will be illustrated in detail in the following description.

DETAILED DESCRIPTION OF THE INVENTION

The present invention refers to a chromatographic separation of regioisomeric mixtures of the metal-phthalocyanines of general formula (I) above reported, by means of a chromatographic separation method performed on a column containing a solid support as stationary phase.

The chromatographic separation method according to the present invention is preferably selected from the group consisting of high pressure liquid chromatography (HPLC) and preparative medium pressure liquid chromatography (MPLC). The HPLC methods of possible use according to the invention may be chosen, for example, from Normal Phase HPLC (NP-HPLC), Reverse Phase HPLC (RP-HPLC) and ION PAIR Reverse Phase HPLC (ION PAIR RP-HPLC).

According to a preferred embodiment of the present invention the solid support to be used as stationary phase is selected from the group consisting of aluminium oxide, silica and silica on which aliphatic and/or aromatic groups are bonded, such as octyl, octadecyl and equi-molar quantities of phenyl and hexyl, commonly named as $C_8$ bonded silica phase, $C_{18}$ bonded silica phase and phenyl/hexyl bonded silica phase.

The separation column is eluted with the mobile phase comprising an organic solvent, preferably selected from the group consisting of dichloromethane, tetrahydrofurane, water, methanol, n-hexane, acetonitrile and mixtures thereof. When ION PAIR RP-HPLC method is performed according to the present invention, an ion pair reagent is added to the mobile phase, such as sodium penthane sulphonate.

According to a particular embodiment of the present invention, the isomeric mixtures of the present phtalocyanines of formula (I) are first dissolved in the initial eluent, preferably consisting of the mixture $H_2Cl_2$:THF:MeOH 94:5:1; the so obtained solution is then applied to the column and the separation is carried out by eluting the column with a mobile phase having a composition which preferably varies for the duration of the chromatographic separation; for example, the following elution system comprising two eluents A and B and having the following elution gradient may be used:

eluent A=$CH_2Cl_2$:THF:MeOH 94:5:1;
eluent B=n-hexane;
gradient timetable (eluent B %): 60-30% in 15 minutes, 30-0% in 5 minutes, 0% for 10 minutes.

According to the present invention, commercially available normal or reverse stationary phases, HPLC grade or anhydrous solvents may be used to perform the present separation process by using HPLC and MPLC.

Regioisomeric mixtures of Zn(II)-phthalocyanines are preferably subjected to the present separation process.

According to a preferred embodiment of the present process regioisomeric mixtures of 1(4),8(11),15(18),22(25) amino and ammonium tetra-substituted Zn(II) phthalocyanines of formula (I) are subjected to the present process, wherein X is preferably selected from between O and S, Z is preferably phenyl, and Y and Y' are preferably selected from methyl and ethyl.

By subjecting to the present process isomeric mixtures of the metal phtalocyanines of formula (I), the corresponding separated isomers $C_{4h}$ and $D_{2h}$ in substantially pure form and the other separated isomers $C_{2v}$ and $C_s$, or a mixture of these isomers $C_{2v}$ and $C_s$, in substantially pure form, are obtained.

The centrosimmetrical metal phtalocyanines of formula (I) in the form of regioisomeric mixtures used in the process according to the present invention, i.e. the compounds of formula (I) wherein, when n=1, R=$R_2$ and $R_1$=$R_3$, and the compounds of formula (I) wherein, when n=0, $R_2$ is H and $R_3$=$R_1$, may be prepared as described in U.S. Pat. No. 5,965,598, which we incorporate herewith by reference; whereas the present non-centrosymmetrical metal phtalocyanines of formula (I), i.e. the present compounds of formula (I) with the exclusion of the above mentioned centrosymmetrical compounds, may be prepared as described in the European Patent Application No. 01106411.0, which we incorporate herewith by reference.

The separated isomers were characterized and unambiguously identified on the basis of TLC, mass spectrometry, UV-Vis spectrometry and $^1$H-NMR.

EXAMPLE 1

Regioisomeric separation of 1(4),8(11),15(18),22 (25)-tetrakis[(3-(dimethylamino) phenoxy) phthalocyaninato] zinc(II) (Compound 1)

70 mg of compound 1(4),8(11),15(18),22(25)-tetrakis[(3-(dimethylamino)phenoxy) phthalocyaninato] zinc(II) (compound 1) prepared as described in U.S. Pat. No. 5,965,598 were dissolved in 15 ml of initial eluent consisting in the mixture $CH_2Cl_2$:THF:MeOH 94:5:1, and loaded into a LiChroprep Si6O (12-25 µm) silica (Merck) column (460× 26 mm), then eluted by using the following elution gradient system at 46 ml min$^{-1}$ with a MPLC system:

eluent A=$CH_2Cl_2$:THF:MeOH 94:5:1;
eluent B=n-hexane;
gradient timetable (eluent B %): 60-30% in 15 min, 30-0% in 5 min, 0% for 10 min.

Three fractions were collected and further purified by MPLC runs with slightly different elution programs:

first fraction (B %): 60-30% in 10 min, 30-0% in 5 min, 0% for 10 min;

second fraction (B %): 50-30% in 5 min, 30-0% in 5 min, 0% for 10 min;

third fraction (B %): 30% for 5 min, 30-0% in 5 min, 0% for 10 min.

Figure 1:
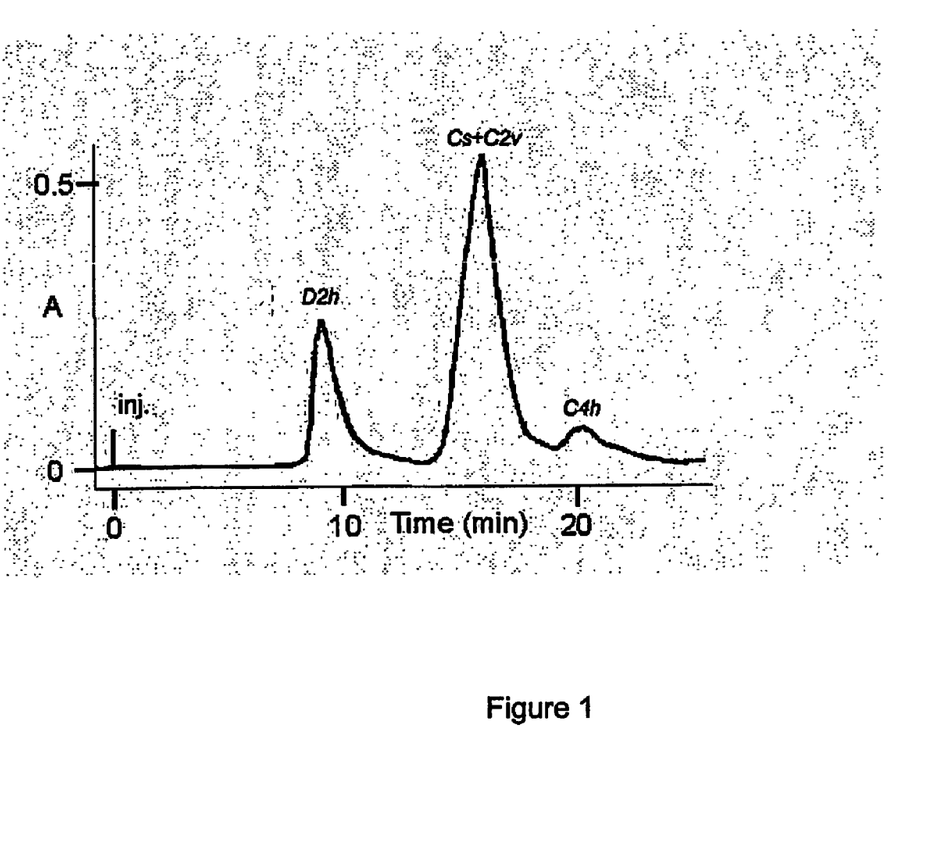
FIG. 1 represents the MPLC chromatogram for the seperation of the tetrasubstituted Zn(II) phthalocyanine compound 1 (isomeric mixture), obtained in the operative conditions described in Example 1.

The MPLC chromatogram of compound 1 is reported in FIG. 1.

Figure 5:
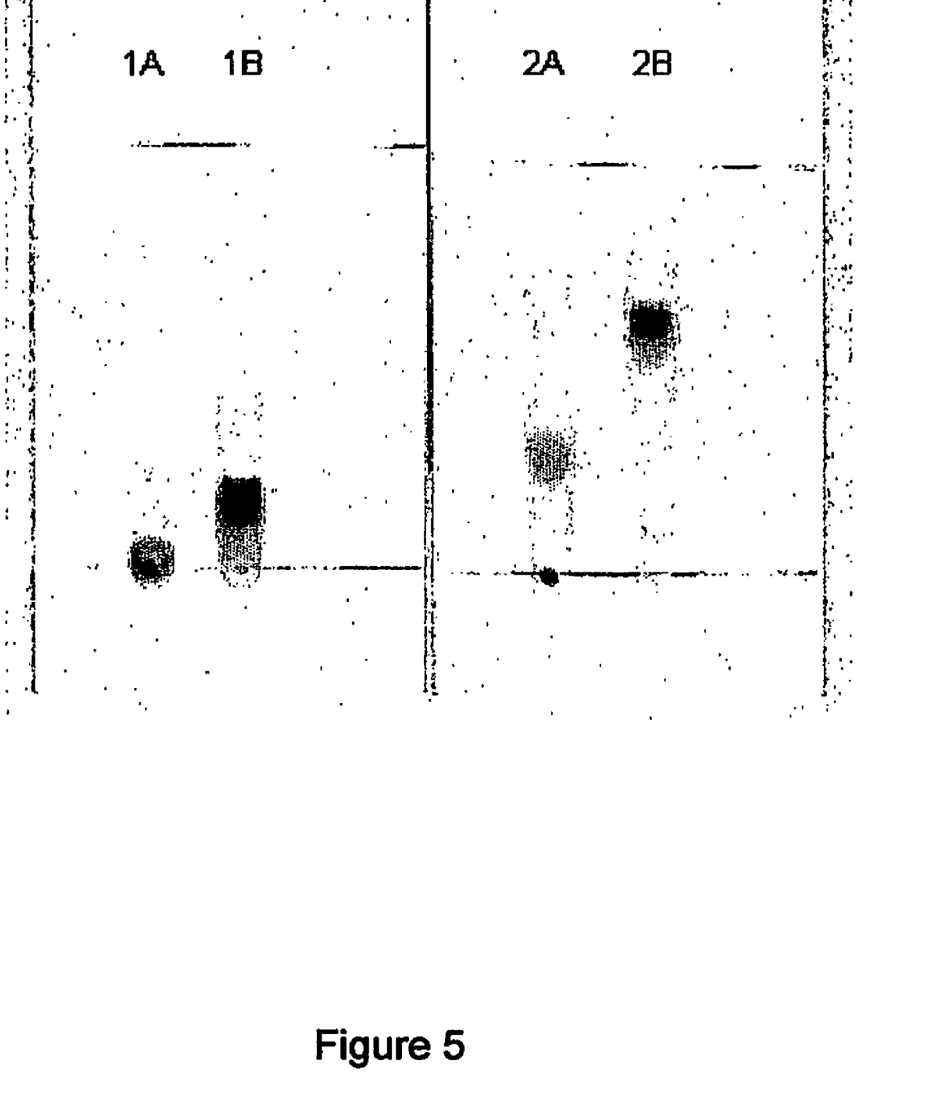
FIG. 5 shows the TLC of compounds 1 (lane A) and 4 (lane B) on Alugram Sil G/UV$_{254}$ (thickness 0.20 mm) with the following eluents:
Eluent 1: 73% CH$_2$Cl$_2$, 24% n-hexane, 2% THF and 0.5% MeOH;
Eluent 2: 71% CH$_2$Cl$_2$, 24% n-hexane, 4% THF and 1% MeOH.
Figure 6:
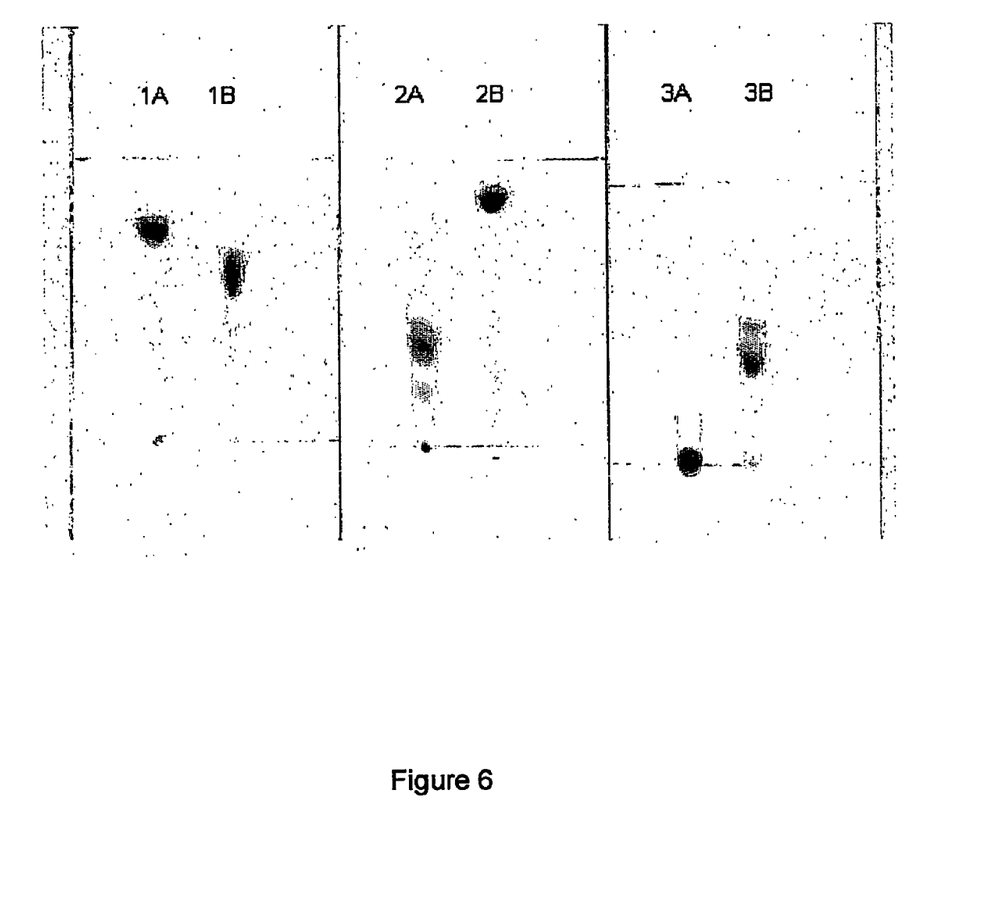
FIG. 6 shows the TLC of compounds 1 (lane A) and 5 (lane B) on Alugram Sil G/UV$_2$54 (thickness 0.20 mm) with the following eluents:
Eluent 1: 60% n-hexane—THF 40%.
Eluent 2: 71% CH$_2$Cl$_2$, 24% n-hexane, 4% THF and 1% MeOH.
Eluent 3: 73% CH$_2$Cl$_2$, 24% n-hexane, 2% THF and 0.5% MeOH.

The initial isomeric mixture as well as the present purification process were assessed by using TLC, HPLC and ESI-MS systems in the following operative conditions:

TLC: Alugram Sil G/UV$_{254}$ (thickness 0.20 mm); eluent: 71% $CH_2Cl_2$, 24% n-hexane, 4% THF and 1% MeOH; spots Rf: 0.75, 0.70 ($D_{2h}$), 0.55, 0.36($C_s$+$C_{2v}$), 0.24 ($C_{4h}$), 0.15. The TLC is reported on the right part of FIG. 5 (lane 2A).

Figure 2:
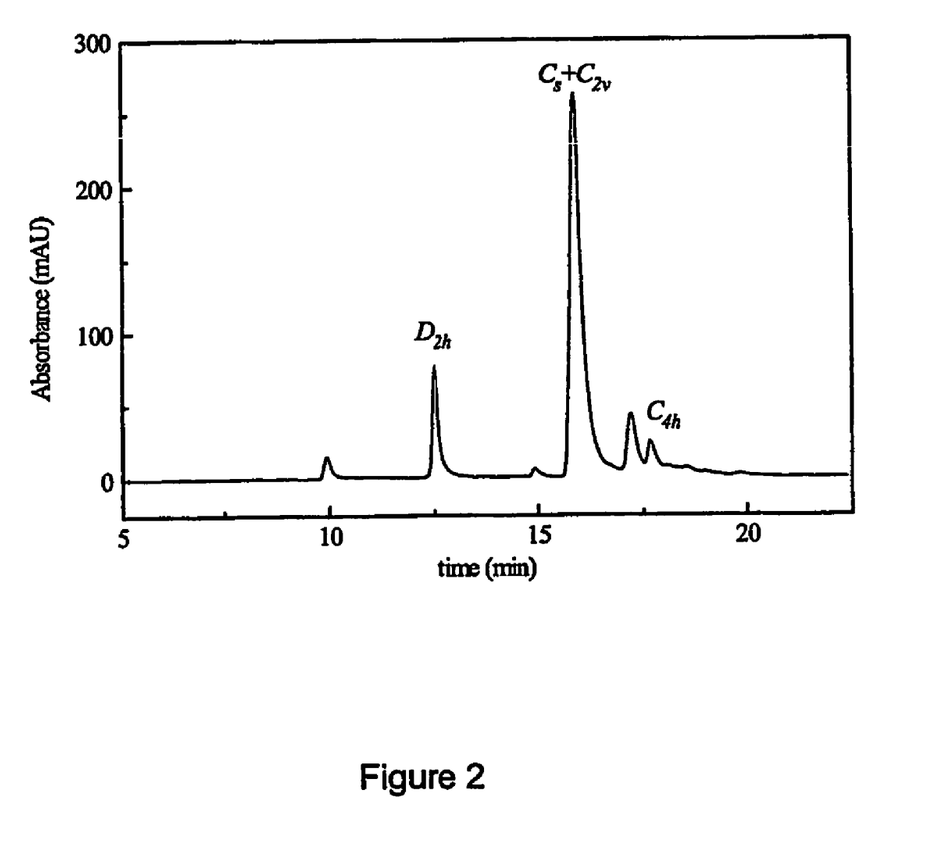
FIG. 2 represents the HPLC chromatogram of compound 1 (isomeric mixture); obtained in the conditions described in Example 1.

HPLC on Zorbax RXSIL (4.6×25 mm) column; eluent gradient timetable (B %): 60-40% in 10 min, 40-0% in 5 min (same eluents used for the above MPLC separation); flow: 1 ml min$^{-1}$; injection: 5 µl of a 0.2 mg/ml solution of compound 1 in initial eluent. The HPLC chromatogram of compound 1 (isomeric mixture) is reported in FIG. 2.

ESI-MS: API 365 PESCIEX mass spectrometer (5 μl/min infusion). The m/z values for [M+H]$^+$ of the four isomers of compound 1 are reported in the following Table 1:

TABLE 1

| Isomer | $D_{2h}$ | $C_s + C_{2v}$ | $C_{4h}$ |
|--------|----------|----------------|----------|
| m/z    | 1119.5   | 1119.5         | 1119.5   |

The UV-Vis spectra have been also recorded in DMF solutions for the four isomers of compound 1; in the following Table 2 the $\lambda_{max}$ (nm) values of the Q-band are reported:

TABLE 2

| Isomer | $D_{2h}$ | $C_s + C_{2v}$ | $C_{4h}$ |
|--------|----------|----------------|----------|
| $\lambda_{max}$ (nm) | 691 | 697 | 702 |

Figure 3:
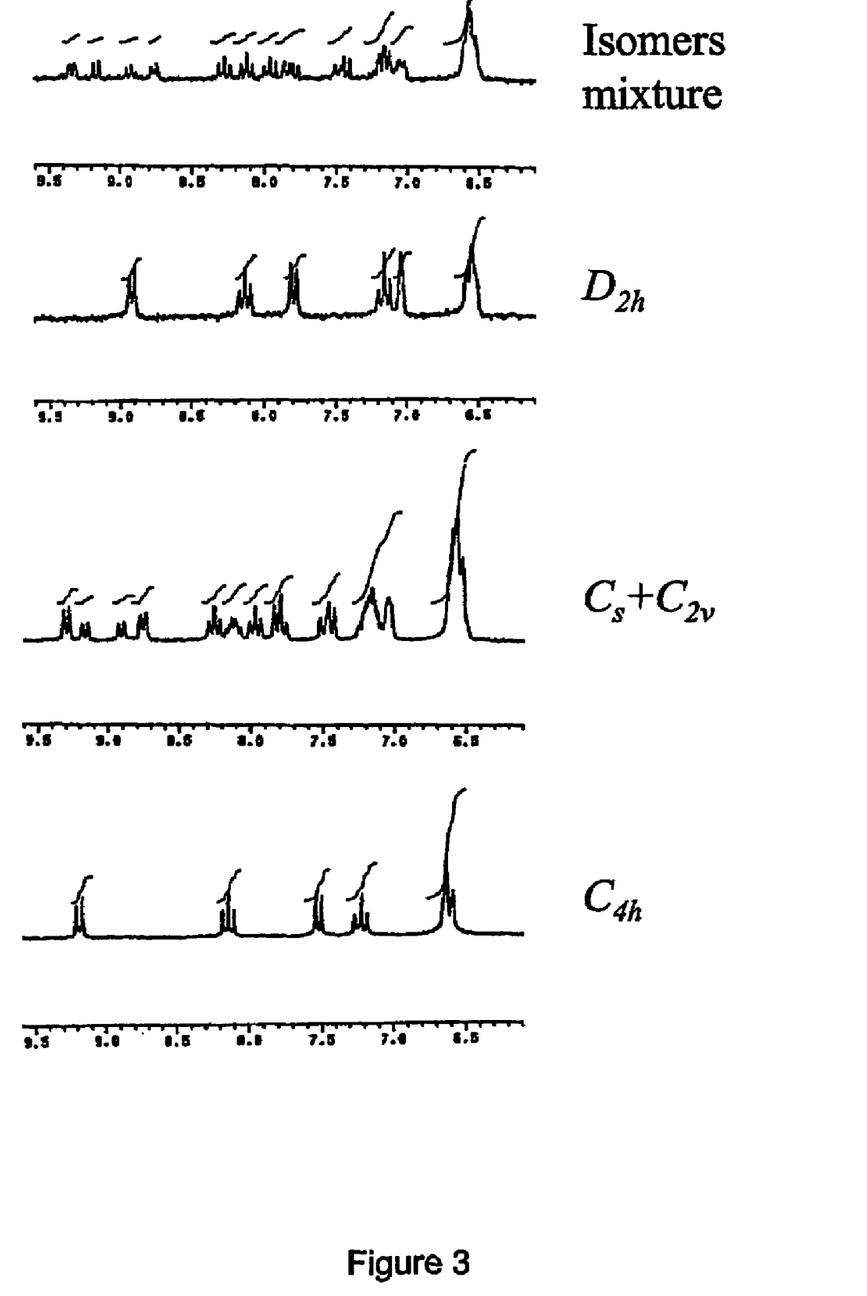
FIG. 3 shows the $^1$H-NMR spectra (particular of the resonance range of the aromatic protons) of compound 1 (isomeric mixture) and of the isomers separated by MPLC as described in Example 1; the spectra were recorded in approximately 1 mg ml$^{-1}$ solutions in [d$_6$]DMSO, by using a Bruker Spectrometer 200 MHz analysis.
Figure 4:
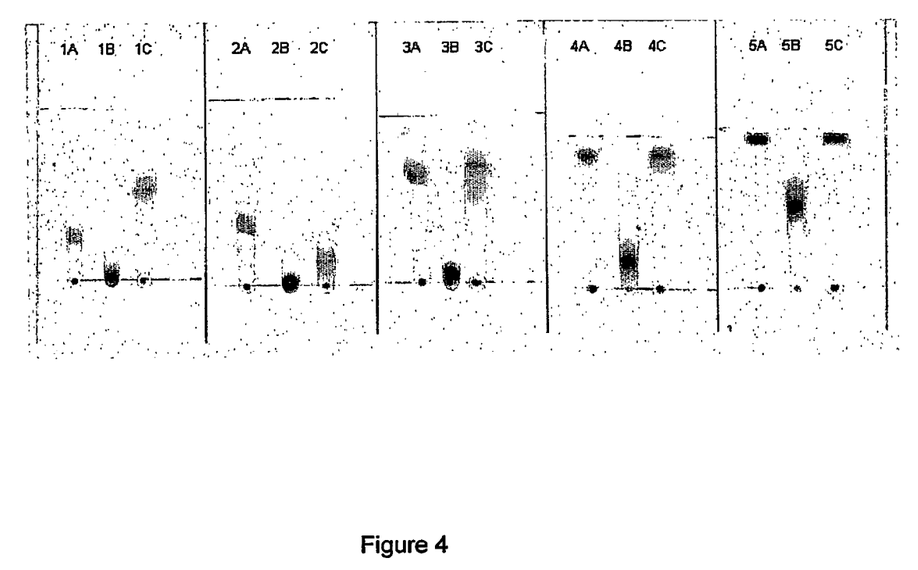
FIG. 4 shows the TLC of compounds 1 (lane A), 2 (lane B) and 3 (lane C) on Alugram Sil G/UV$_{254}$ (thickness 0.20 mm) with the following eluents:
Eluent 1: 60% n-hexane—THF 40%.
Eluent 2: 71% CH$_2$Cl$_2$, 24% n-hexane, 4% THF and 1% MeOH.
Eluent 3: 66% CH$_2$Cl$_2$, 25% n-hexane, 6.5% THF and 2.5% MeOH.
Eluent 4: 65.5% CH$_2$Cl$_2$, 25% n-hexane, 8% THF and 1.5% MeOH.
Eluent 5: 60% CH$_2$Cl$_2$, 25% n-hexane, 12.5% THF and 2.5% MeOH

$^1$H-NMR spectra of compound 1 (isomeric mixture) and of the MPLC separated isomers was also recorded in approximately 1 mg ml$^{-1}$ solutions in [d$_6$]DMSO, by using a Bruker Spectrometer 200 MHz analysis. In FIG. 3 the resonance range of the aromatic protons in these spectra has been reported.

The $^1$H-NMR data of the four isomers of compound 1 are reported in the following Table 3, wherein H'=proton of $C_s$ isomer, and H"=proton of $C_{2v}$ isomer.

TABLE 3

| Isomer | $D_{2h}$ | $C_s + C_{2v}$ | $C_{4h}$ |
|--------|----------|----------------|----------|
| δ(H$^b$/H$^{b^1}$) | 8.91(d, $^3$J=7.4Hz, 4H) | 9.30(d, $^3$J=7.4Hz, H'+2H")<br>9.16(d, $^3$J=7.4Hz, H')<br>8.91(d, $^3$J=7.4Hz, H')<br>8.75(d, $^3$J=7.4Hz, H'+2H") | 9.17(d, $^3$J=7.4Hz, 4H) |
| δ(H$^{a^1}$) | 8.12(dd, $^3$J=7.4Hz, 4H) | 8.29-8.22(dd, $^3$J=7.4Hz, H'+2H")<br>8.17-8.07(m, 2H')<br>8.01-7.93(dd, $^3$J=7.4Hz, H'+2H") | 8.13(dd, $^3$J=7.4Hz, 4H) |
| δ(H$^a$) | 7.78(d, $^3$J=7.4Hz, 4H) | 7.84-7.75(m, 2H'+2H")<br>7.52-7.42(m, 2H'+2H") | 7.51(d, $^3$J=7.4Hz, 4H) |
| δ(H$^e$) | 7.15(dd, $^3$J=8.1Hz, 4H) | 7.25-7.09(m, 4H'+4H") | 7.21(dd, $^3$J=8.1Hz, 4H) |
| δ(H$^c$) | 7.03(s, 4H) | 7.09-7.01(m, 2H'+2H")<br>6.62-6.50(m, 2H'+2H") | 6.58(s, 4H) |
| δ(H$^d$, H$^f$) | 6.60-6.50(m, 8H) | 7.09-7.01(m, 4H'+4H")<br>6.62-6.50(m, 4H'+4H") | 6.66-6.56(m, 8H) |
| δ(H$^m$) | 3.05(s, 24H) | 3.07-2.85(m, 24H'+24H") | 2.87(s, 24H) |

EXAMPLE 2

It is reported the TLC separation (on silica sheets Alugram SilG) of the isomers of the following compounds:
  1(4),8(11),15(18),22(25)-tetrakis[(3-(dimethylamino) phenoxy) phthalocyaninato] zinc(II) (compound 1);
  1(4),8(11),15(18),22(25)-tetrakis[(4-(dimethylamino) phenoxy) phthalocyaninato] zinc(II) (compound 2);
  1(4),8(11),15(18),22(25)tetrakis[(2-(dimethylamino)phenoxy) phthalocyaninato] zinc(II) (compound 3).

The compounds 1, 2 and 3 are prepared as described in U.S. Pat. No. 5,965,598 and show a difference in the position of the dimethylamino groups on the peripheral phenoxy rings. Mixtures of tetrahydrofurane/n-hexane and dichloromethane/n-hexane/tetrahydrofurane/methanol are used as mobile phases. The optimal eluent for compound 1, as reported in Example 1, is constituted by 71% CH$_2$Cl$_2$, 24% n-hexane, 4% THF and 1% MeOH. Three major spots are observed with the following retention factors (Rf): 0.70 (D$_{2h}$), 0.36(C$_s$+C$_{2v}$), 0.24 (C$_{4h}$).

The optimal eluent for compound 2 is composed by 60% CH$_2$Cl$_2$, 25% n-hexane, 12.5% THF and 2.5% MeOH. Three major spots are observed with the following retention factors (Rf): 0.85, 0.58 and 0.40.

The compound 3 shows separated spots with 60% n-hexane—THF 40% (Rf 0.60, 0.52, 0.47) and with 60% CH$_2$Cl$_2$, 37.5% n-hexane, 2% THF and 0.5% MeOH. The major spots observed have the following retention factors (Rf): 0.30, 0.21 and 0.15.

EXAMPLE 3

It is reported the TLC separation (on silica sheets Alugram SilG) of the isomers of the following compounds:
  1(4),8(11),15(18),22(25)-tetrakis[(3-(dimethylamino) phenoxy) phthalocyaninato] zinc(II) (compound 1);
  1(4),8(11),15(18),22(25)-tetrakis[(4-(diethylamino)phenoxy) phthalocyaninato] zinc(II) (compound 4).

The compounds 1 and 4 are prepared as described in U.S. Pat. No. 5,965,598 and are representative of the variation of the alkyl substituents of the amino groups. Mixtures of dichloromethane/n-hexane/tetrahydrofurane/methanol are used as mobile phases.

The optimal eluent for the compound 1, as reported in Example 1, is constituted by 71% CH$_2$Cl$_2$, 24% n-hexane, 4% THF and 1% MeOH. Three major spots are observed with the following retention factors (Rf): 0.70 (D$_{2h}$), 0.36 (C$_s$+C$_{2v}$), 0.24 (C$_{4h}$).

This eluent is also the optimal one for the separation of compound 4 (Rf values: 0.76, 0.59, 0.52); however a good chromatographic result is obtained also with a mixture of 73% CH$_2$Cl$_2$, 24% n-hexane, 2% THF and 0.3% MeOH (Rf: 0.35, 0.17, 0.08).

EXAMPLE 4

It is reported the TLC separation (on silica sheets Alugram SilG) of the isomers of the following compounds:
  1(4),8(11),15(18),22(25)tetrakis[(3-(dimethylamino)phenoxy) phthalocyaninato] zinc(II) (compound 1);

1(4),8(11),15(18),22(25)-tetrakis[((3-(dimethylamino) phenyl)sulfanyl) phthalocyaninato] zinc(II) (compound 5).

The compounds 1 and 5 have been prepared as described in U.S. Pat. No. 5,965,598 and are representative of the variation of the bridging atom between phthalocyanine ring and phenyl substituent group. Mixtures of tetrahydrofurane/n-hexane and dichloromethane/n-hexane/tetrahydrofurane/methanol are used as mobile phases.

The optimal eluent for the compound 1, as reported in Example 1, is constituted by 71% $CH_2Cl_2$, 24% n-hexane, 4% THF and 1% MeOH. Three major spots are observed with the following retention factors (Rf): 0.70 ($D_{2h}$), 0.36 ($C_s+C_{2v}$), 0.24 ($C_{4h}$).

The optimal eluent for the compound 5 is constituted by 73% $CH_2Cl_2$, 24% n-hexane, 2% THF and 0.5% MeOH (Rf: 0.49, 0.36, 0.30).

EXAMPLE 5

Regoisomeric separation of 1(4),8(11),15(18),22 (25)-tetrakisr3-(dimethylamino) phenoxy) phthalocyaninatol zinc(II) (Compound 1) by Means of RP-HPLC on C18 column Regioisomeric separation for compound 1 was performed also by RP-HPLC by the means of a C18 column having the following characteristics: Phenomenex LUNA C18 column (4.6×150 mm, 5 μm particle size); column temperature, room temperature; flow rate, 1 m/min; isocratic elution with MeOH; injection volume, 10 μl; samples dissolved in MeOH/DMF (9-1, v/v); λ of 695±20 nm for isomer quantification, 254 nm for purity analysis and a λ range of 190-800 nm for qualitative analysis.

The elution order was the same observed in NP-HPLC, indicating a separation driven by steric hindrance: molecules without faced substituent groups and thus higher planarity were more retained.

Figure 7:
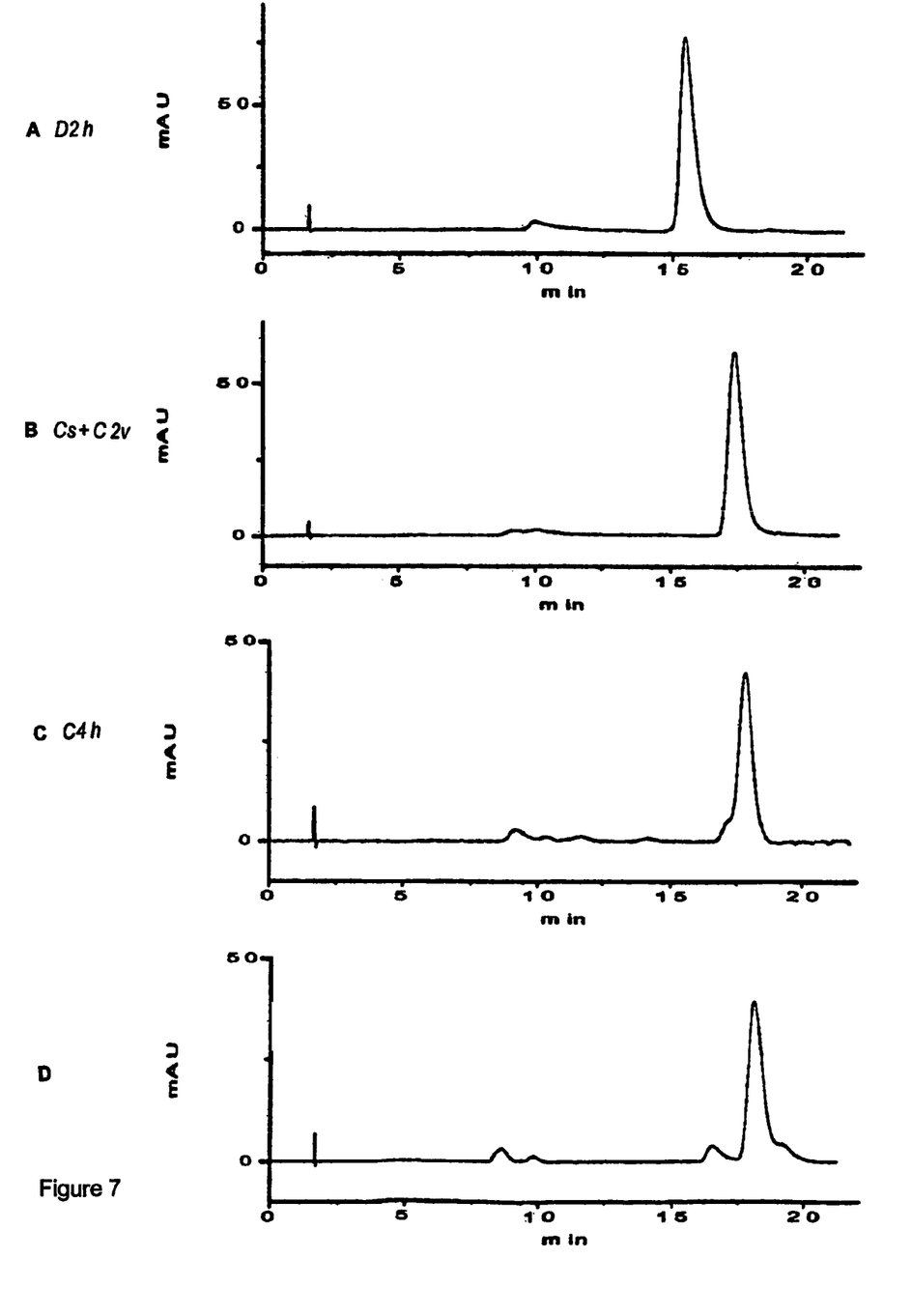
FIG. 7 represents the RP-HPLC chromatograms for the separation of the tetrasubstituted Zn(II) phthalocyanine compound 1 (isomeric mixture), obtained in the operative conditions described in Example 5, wherein: (A) is D$_{2h}$ isomer purified by MPLC (60 ng/μl), (B) is isomers C$_s$+C$_{2v}$ purified by MPLC (47.5 ng/μl), (C) is C$_{4h}$ isomer purified by MPLC (50 ng/μl), and (D) is the mixture obtained in DMF as solvent.

The assignation of HPLC peaks was made by standard adds of the pure isomers (previously separated by preparative MPLC) and from the UV-Vis spectra of the chromatographic peaks. In FIG. 7 are showed RP-HPLC chromatograms for MPLC purified isomers and for a mixture synthesized in DMF as solvent. Chromatographic parameters on LUNA C18 column are reported in the following Table 4, wherein the mean retention times were calculated with n=10, and the column dead time was measured by the positive peak of DMF.

TABLE 4

| Isomer | Rt (min) | k' | Slope (mAU · μl/ng) | Intercept (mAU) | $R^2$ |
|---|---|---|---|---|---|
| $D_{2h}$ | 15.7 ± 0.2 | 8.29 | 50.9 ± 0.4 | −47 ± 18 | >0.999 |
| $C_s + C_{2v}$ | 17.5 ± 0.1 | 9.36 | 49.8 ± 0.5 | −30 ± 20 | >0.999 |
| $C_{4h}$ | 17.8 ± 0.1 | 9.53 | 48.4 ± 0.3 | −42 ± 15 | >0.999 |

All the injected solutions were made in MeOH/DMF (9-1, v/v), except the $D_{2h}$ isomer ones that, due to its lower solubility in MeOH, were made in MeOH/DMF (1-1, v/v). Linearity has been verified for each isomer with a 6 points calibration in the range 0.5-100 ng/μl (each solution was tested three times). The separated isomers displayed very similar calibration slopes; this indicate that the collection of the entire phthalocyanine Q-band (695±20 nm) lead to a reliable relative quantification of the isomers in complex mixtures. In fact the use of this long wavelength detection, were the molecule posses a very high extinction coefficient (ε=3·10⁵ M/cm), lowers interferences and enhances sensitivity (calibration slopes are 2.49 fold higher than the ones found with a 254 nm detection). LOD and LOQ, calculated respectively with a signal-to-noise ratio of 3:1 and 10:1, were 0.4 ng/μl and 1.2 ng/μl.

The separation method reported above can be easily transferred to a preparative scale, i.e. by a MPLC separation, by means of procedures well-known in the art.

EXAMPLE 6

Regioisomeric separation of 1(4),8(11),15(18),22 (25)-tetrakis[(3-dimethylamino-phenoxy)phthalocyaninato]zinc(II) (compound 1) isomers by means of RP-HPLC on a Phenyl-Hexyl column Isomers separation for compound 1 by RP-HPLC was improved by the means of a Phenyl-Hexyl column having the following parameters: Phenomenex LUNA Phenyl-Hexyl column (4.6×150 mm, 5 μm particle size); column temperature, 15, 20 or 30° C.; flow rate, 1 ml/min; eluent, isocratic elution with mixtures $MeOH/CH_3CN/CH_2Cl_2$ or $MeOH/CH_3CN/THF$ (see table 4); injection volume, 10 μl; samples dissolved in eluent; λ of 695±20 nm for isomer quantification, 254 nm for purity analysis and a λ range of 190-800 nm for qualitative analysis.

The elution order was, again, the same observed in NP-HPLC, indicating a separation driven by steric hindrance.

Figure 8:
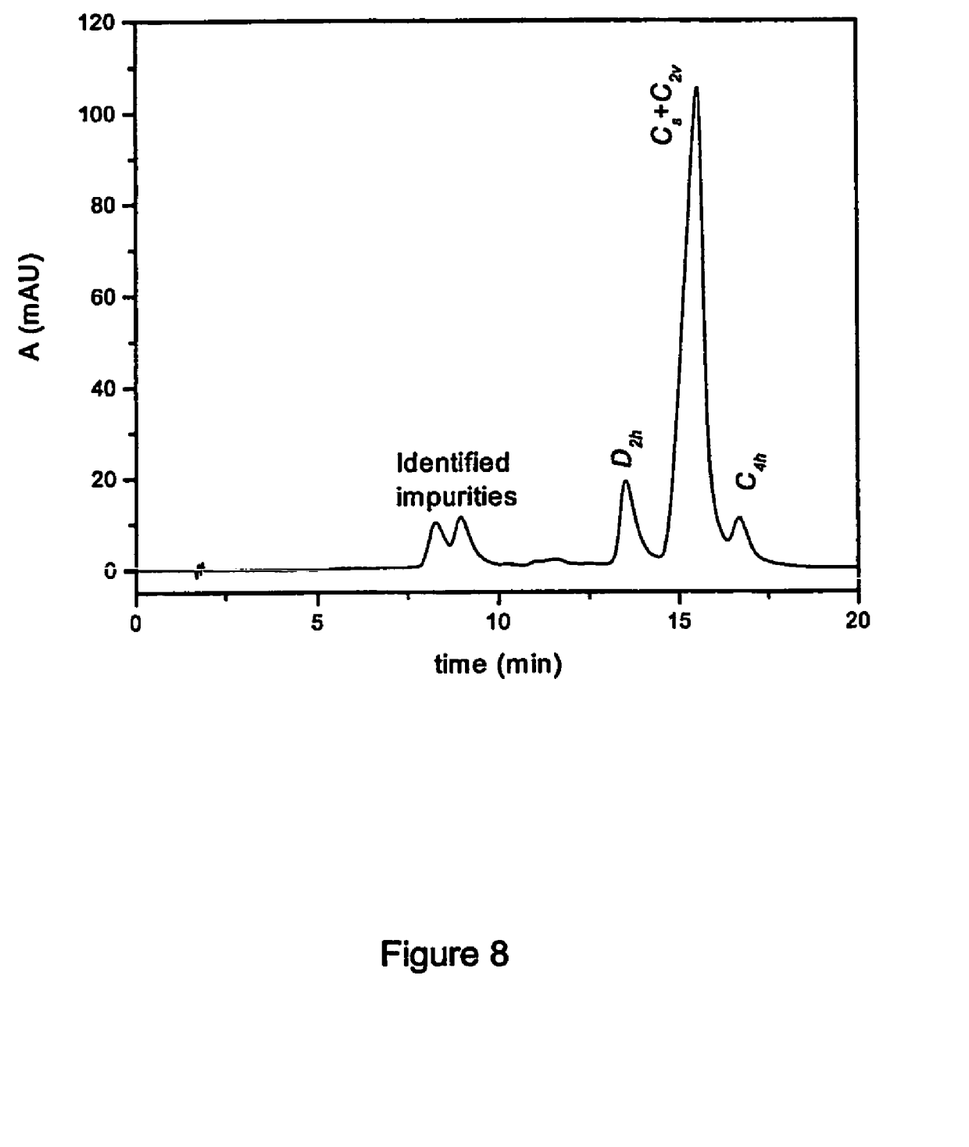
FIG. 8 shows RP-HPLC chnromatogram on Phenyl-Hexyl column for the separation of the tetrasubstituted Zn(II) phthalocyanine compound 1 (isomeric mixture).

The assignation of HPLC peaks was made by standard adds of the pure isomers (previously separated by preparative MPLC) and from the UV-Vis spectra of the chromatographic peaks. FIG. 8 shows a HPLC chromatogram for the isomeric mixture for compound 1 synthesized in DMF as solvent.

RP-HPLC chromatographic parameters on LUNA Phenyl-Hexyl column are reported in the following Table 5.

TABLE 5

| Eluent composition | T (° C.) | RT (min) $D_{2h}$ isomer | RT (min) $C_s + C_{2v}$ isomers | RT (min) $C_{4h}$ isomer |
|---|---|---|---|---|
| $MeOH/CH_3CN/THF$ (80/12.5/7.5, v/v/v) | 20 | 16.3 | 17.8 | 18.5 |
| $MeOH/CH_3CN/THF$ (67.5/25/7.5, v/v/v) | 20 | 11.6 | 13.0 | 13.8 |
| $MeOH/CH_3CN/THF$ (70/25/5, v/v/v) | 20 | 14.8 | 16.6 | 17.8 |
| $MeOH/CH_3CN/THF$ (70/25/5, v/v/v) | 30 | 11.9 | 13.4 | 14.4 |
| $MeOH/CH_3CN/THF$ (48/48/4, v/v/v) | 30 | 9.9 | 11.9 | 13.4 |
| $MeOH/CH_3CN/CH_2Cl_2$ (70/25/5, v/v/v) | 30 | 13.6 | 15.7 | 16.9 |
| $MeOH/CH_3CN/$ $CH_2Cl_2$ (70/25/5, v/v/v) | 15 | 19.4 | 22.2 | 23.9 |

EXAMPLE 7

Regioisomeric separation of 1(4),8(11),15(18),22 (25)-tetrakis[(3-(dimethylamino)phenoxy)phthalocyaninato]zinc(II) (compound 1) by Means of ION PAIR RP-HPLC Isomers separation for compound 1 by RP-HPLC was also achieved using a C18 column having the following parameters: Phenomenex LUNA C18 column (4.6×150 mm, 5 μm particle size); column temperature, 25° C.; flow rate, 1 ml/min; isocratic elution with an eluent containing an ion pair reagent, such as the mixture sodium pentanesulfonate 60 mM in water (buffered at pH 3 with phosphate 10 mM)/MeOH/THF (20/48/32, v/v/v); injection volume, 20 μl; samples dissolved in eluent; detection λ, 254±20 nm e 695±20 nm and a λ range of 190-800 nm for qualitative analysis.

The elution order was $C_{4h}$ isomer, $C_s+C_{2v}$ isomers mixture and $D_{2h}$ isomer. That means that isomers with amino groups more accessible to the ion pair reagent were more retained.

Figure 9:
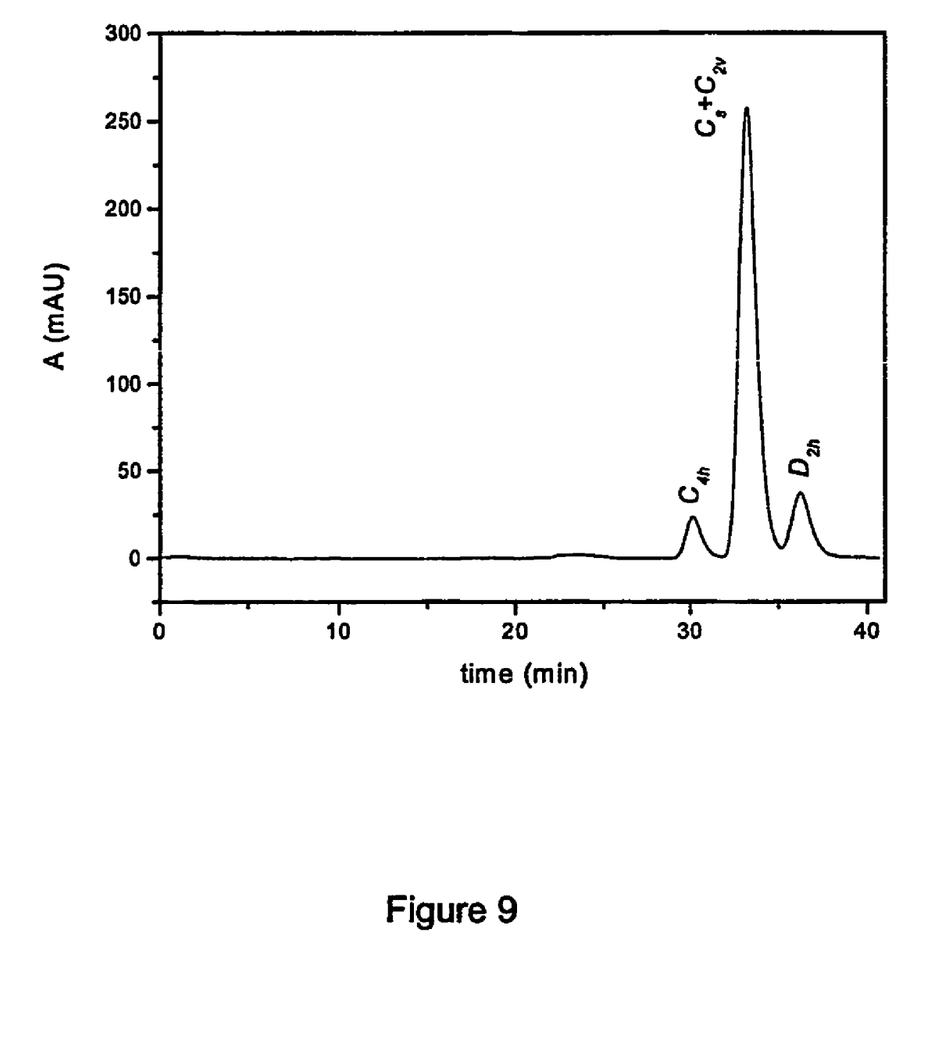
FIG. 9 shows ION PAIR RP-HPLC chromatogram for the separation of the tetrasubstituted Zn(II) phthalocyanine compound 1 (isomeric mixture).

The assignation of HPLC peaks was made by standard adds of the pure isomers (previously separated by preparative MPLC) and from the UV-Vis spectra of the 5 chromatographic peaks. FIG. 9 shows a HPLC chromatogram for the isomeric mixture for compound 1 synthesized in DMF as solvent.

ION PAIR RP-HPLC on C18 column chromatographic parameters for compound 1 isomers are reported in the following Table 6.

TABLE 6

| Isomer | RT (min) | RRT | $\lambda_{max}$ (nm) |
|---|---|---|---|
| $C_{4h}$ | 30.1 | 0.91 | 702 |
| $C_s + C_{2v}$ | 33.2 | 1.00 | 694 |
| $D_{2h}$ | 36.0 | 1.08 | 690 |

EXAMPLE 8

Regioisomeric separation of 1(4),8(11),15(18),22(25)-tetrakis[(3-(trimethyl ammonium)phenoxy)phtalocyaninato]zinc(II) (compound 6) by Means of ION PAIR RP-HPLC Complete isomers separation for the tetracationic phtalocyanine derivative compound 6 prepared as described in U.S. Pat. No. 5,965,598 by RP-HPLC was performed using a C18 column having the following parameters: Phenomenex LUNA C18 column (4.6×150 mm, 5 μm particle size); column temperature, 35° C.; flow rate, 1 ml/min; isocratic elution with an eluent containing an ion pair reagent, such as the mixture sodium pentanesulfonate 120 mM in water (buffered at pH 3 with phosphate 10 mM)/MeOH (35/65, v/v); injection volume, 10 μl; samples dissolved in eluent; detection λ, 254±20 nm e 695±20 nm and a λ range of 190-800 nm for qualitative analysis.

The elution has led to a complete isomers separation, and the elution order was $C_{4h}$ isomer, $D_{2h}$ isomer, $C_s$ isomer and $C_{2v}$ isomer.

Figure 10:
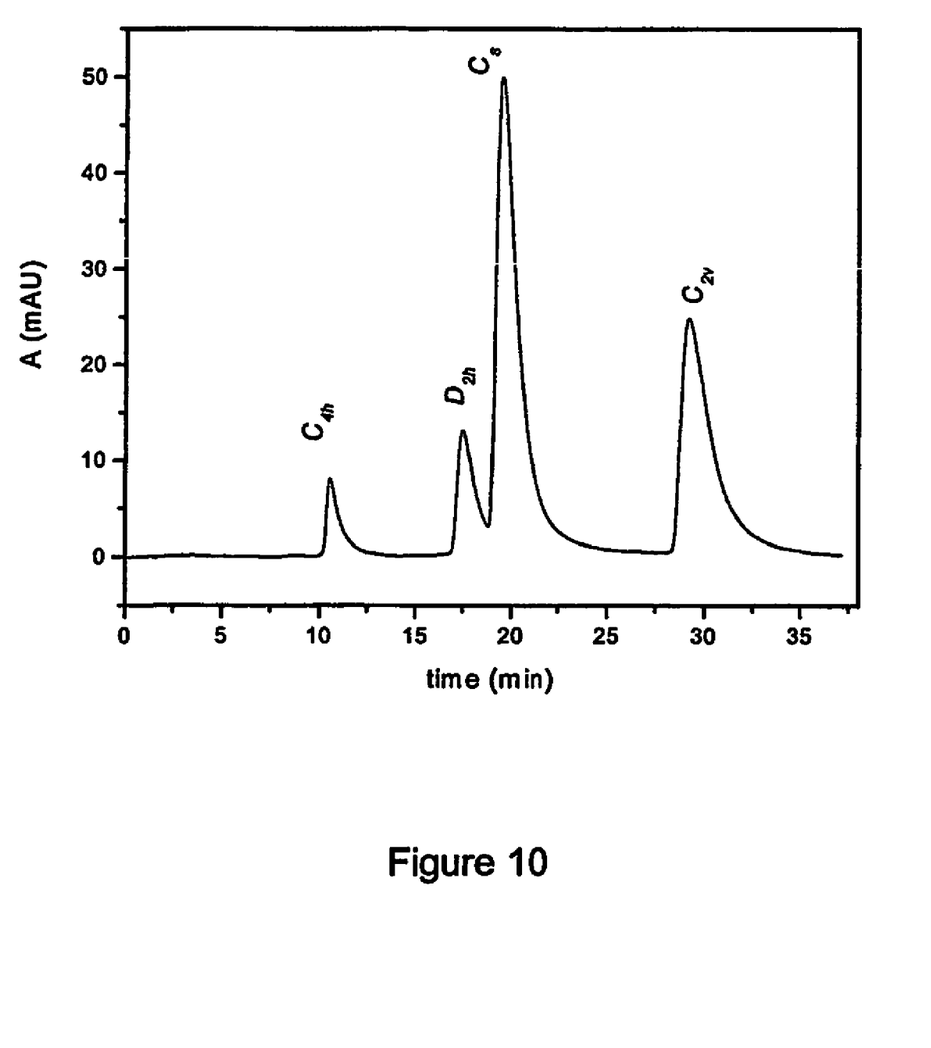
FIG. 10 shows ION PAIR RP-HPLC chromatogram for the separation of the tetrasubstituted Zn(II) phthalocyanine compound 6 (isomeric mixture).

The assignment of HPLC peaks was made by standard adds of the pure isomers (previously separated in the non cationic compound 1 by preparative MPLC and alkylated with MeI), by comparison with $^1$H-NMR spectra and from the UV-Vis spectra of the chromatographic peaks. FIG. 10 shows a HPLC chromatogram for a compound 6 mixture.

ION PAIR RP-HPLC on C18 column chromatographic parameters for compound 6 isomers are reported in the following Table 7.

TABLE 7

| Isomer | RT (min) | RRT | $\lambda_{max}$ (nm) |
|---|---|---|---|
| $C_{4h}$ | 10.6 | 0.54 | 696 |
| $D_{2h}$ | 17.5 | 0.90 | 684 |
| $C_s$ | 19.5 | 1.00 | 688 |
| $C_{2v}$ | 29.2 | 1.50 | 688 |

The Examples reported above show how suitable the present process is for the separation of isomeric mixtures of differently substituted metal phtalocyanines (I); in fact, by using the same solvents or solvents mixture as those used above for TLC separation, an effectual separation of the products above may be carried out also by HPLC and preparative MPLC.

The separated isomers of metal phtalocyanines of formula (I), besides having the advantageous properties of the corresponding isomeric mixtures already reported in the above cited patents in the name of the Applicant, in some cases also possess a molar absorption coefficient and/or wavelength higher than the photosensitizers previously described, as indicated in Table 2 of Example 1; and this represents an important requirement for an effective therapeutic response.

The finding about differential toxicity between host cells and micro-organisms strengthens the importance of the claimed products of formula (1).

The regioisomers of the present phtalocyanines of formula (I) may be therefore used for the same uses already described for the corresponding isomeric mixtures in the above mentioned patents in the name of the Applicant, such as for preparing pharmaceutical compositions, possibly with pharmacologically acceptable excipients and diluents, to be used in photodynamic therapy or as tracers for in vivo/in vitro diagnostics, possibly in combination with a pharmaceutically acceptable carrier.

The invention claimed is:

1. A process for the separation of regioisomeric mixtures of metal phthalocyanines of general formula (I)

wherein
Me is selected from the group consisting of Zn, Si(OR$_4$)$_2$, Ge(OR$_4$)$_2$ and AlOR$_4$, wherein R$_4$ is chosen from the group consisting of H and C$_1$-C$_{15}$ alkyl;
n=0, 1;
R and R$_1$ are selected from substituents of general formula (II)

wherein
X is selected from the group consisting of O, S, NHCO, $-CH_2-$, C=C and C≡C;
Z is selected from phenyl, aryl, arylalkyl and cycloaliphatic groups; and
Y and Y', equal or different from each other, are selected from $C_1$-$C_{15}$ alkyl groups;
q=0, 1;
$R_2$ and $R_3$ are selected from H and substituents of general formula (II) as defined above, with the proviso that:
at least one of $R_2$ and $R_3$ is always other than H; and
when n=0:
a) $R_2$ and $R_3$, same or different from each other, are both different from H, or
b) $R_2$=H and $R_3$ is same or different from $R_1$;
and of pharmaceutically acceptable salts thereof;
said process consisting in a chromatographic separation comprising the following steps:
i) applying the mixture to a separation column containing the stationary phase comprising a solid support;
ii) separating said mixture by eluting the said column with the mobile phase comprising a solvent selected from water, an organic solvent and mixtures thereof, said organic solvent being selected from the group consisting of dichloromethane, tetrahydrofuran, methanol, n-hexane, acetonitrile and mixtures thereof.

2. The process according to claim 1, wherein the said chromatographic separation is performed by a chromatographic method selected from the group consisting of high pressure liquid chromatography (HPLC) and medium pressure liquid chromatography (MPLC).

3. The process according to claim 2, wherein the said high pressure liquid chromatography is selected from the group consisting of Normal Phase HPLC, Reverse Phase HPLC and ION PAIR Reverse Phase HPLC.

4. The process according to claim 1, wherein the said solid support is selected from the group consisting of aluminium oxide, silica and silica on which groups are bonded, said groups being selected from aliphatic groups, aromatic groups and mixtures thereof.

5. The process according to claim 4, wherein said groups are selected from the group consisting of octyl, octadecyl and equi-molar quantities of phenyl and hexyl groups.

6. The process according to claim 1, wherein in the said metal phthalocyanines of formula (I) Me is Zn.

7. The process according to claim 1, wherein in the said metal phthalocyanines of formula (I) n=0, $R_2$=H and $R_1$=$R_3$, X is selected from between O and S, Z is phenyl, and Y and Y' are selected from between methyl and ethyl.

8. The process according to claim 1, wherein the said metal phthalocyanine of formula (I) is 1(4),8(11),15(18),22(25)-tetrakis[(3-(dimethylamino)phenoxy) phthalocyaninato] zinc(II) (compound 1).

9. The process according to claim 1, wherein the said metal phthalocyanine of formula (I) is 1(4),8(11),15(18),22(25)-tetrakis[(4-(dimethylamino)phenoxy) phthalocyaninato] zinc(II) (compound 2).

10. The process according to claim 1, wherein the said metal phthalocyanine of formula (I) is 1(4),8(11),15(18),22(25)-tetrakis[(2-(dimethylamino)phenoxy) phthalocyaninato] zinc(II) (compound 3).

11. The process according to claim 1, wherein the said metal phthalocyanine of formula (I) is 1(4),8(11),15(18),22(25)-tetrakis[(4-(diethylamino)phenoxy) phthalocyaninato] zinc(II) (compound 4).

12. The process according to claim 1, wherein the said metal phthalocyanine of formula (I) is 1(4),8(11),15(18),22(25)-tetrakis[((3-(dimethylamino)phenyl)sulfanyl) phthalocyaninato] zinc(II) (compound 5).

13. The process according to claim 1, wherein the said metal phthalocyanine of formula (I) is 1(4),8(11),15(18),22(25)-tetrakis[(3-(trimethylammonium)phenoxy) phthalocyaninato] zinc(II) (compound 6).

14. Regioisomers of the metal phthalocyanines of formula (I)

wherein
Me is selected from the group consisting of Zn, $Si(OR_4)_2$, $Ge(OR_4)_2$ and $AlOR_4$, wherein $R_4$ is chosen from the group consisting of H and $C_1$-$C_5$ alkyl;
n=0, 1;
R and $R_1$ are selected from substituents of general formula (II)

wherein
X is selected from the group consisting of O, S, NHCO, $-CH_2-$, C=C and C≡C;
Z is selected from phenyl, aryl, arylalkyl and cycloaliphatic groups; and
Y and Y', equal or different from each other, are selected from $C_1$-$C_{15}$ alkyl groups;
q=0, 1;
$R_2$ and $R_3$ are selected from H and substituents of general formula (II) as defined above, with the proviso that:
at least one of $R_2$ and $R_3$ is always other than H; and
when n=0:
a) $R_2$ and $R_3$, same or different from each other, are both different from H, or b) $R_2$=H and $R_3$ is same or different from $R^1$; said regioisomers being in substantially pure form, and represented by:

regioisomer $C_{4h}$;
regioisomer $D_{2h}$;
regioisomer $C_{2v}$;
regioisomer Cs;
mixture of regioisomers $C_{2v}$ and Cs.

15. Pharmaceutical compositions for the photodynamic therapy comprising a regioisomer of metal phthalocyanines of formula (I) as defined in claim 14.

16. Diagnostic agents for the in vivo/in vitro diagnostic use containing as the active principle a regioisomer of metal phthalocyanines of formula (I) as defined in claim 14.

* * * * *